United States Patent [19]

Tabak et al.

[11] Patent Number: 4,504,693
[45] Date of Patent: Mar. 12, 1985

[54] CATALYTIC CONVERSION OF OLEFINS TO HEAVIER HYDROCARBONS

[75] Inventors: Samuel A. Tabak, Wenonah; Bernard S. Wright, East Windsor; Hartley Owen, Belle Mead, all of N.J.

[73] Assignee: Mobil Oil Corporation, New York, N.Y.

[21] Appl. No.: 616,379

[22] Filed: Jun. 1, 1984

[51] Int. Cl.³ .............................................. C07C 2/02
[52] U.S. Cl. .................................... 585/520; 585/533
[58] Field of Search ................................ 585/520, 533

[56] References Cited

U.S. PATENT DOCUMENTS

| | | | |
|---|---|---|---|
| 4,433,185 | 2/1984 | Tabak | 585/312 |
| 4,444,988 | 4/1984 | Capsuto et al. | 585/415 |
| 4,456,779 | 6/1984 | Owen et al. | 585/415 |

*Primary Examiner*—Curtis R. Davis
*Attorney, Agent, or Firm*—Alexander J. McKillop; Michael G. Gilman; L. G. Wise

[57] ABSTRACT

A catalytic process for converting an olefinic feedstock comprising lower olefin to heavier hydrocarbon product comprising the steps of:
  contacting the feedstock and a recycled hydrocarbon with shape-selective zeolite oligomerization catalyst in catalytic reaction zone at elevated temperature and pressure to provide a heavier hydrocarbon effluent stream comprising heavy, intermediate and light hydrocarbons;
  flashing the effluent stream between the reaction zone and a phase separation zone by reducing pressure of the effluent stream, thereby producing a heavy liquid stream rich in heavy hydrocarbons and a flashed effluent vapor stream containing lighter hydrocarbons;
  separating and recovering a recycle stream rich in intermediate range hydrocarbons from the separation zone and pressurizing the recycle stream for recycle to the reactor inlet;
  further fractionating the heavy liquid stream and flashed effluent vapor from the phase separation zone in first distillation tower to remove light hydrocarbons therefrom; and
  recovering substantially all of the heavy hydrocarbons produced in the reaction zone in a fractionated liquid product stream.

10 Claims, 1 Drawing Figure

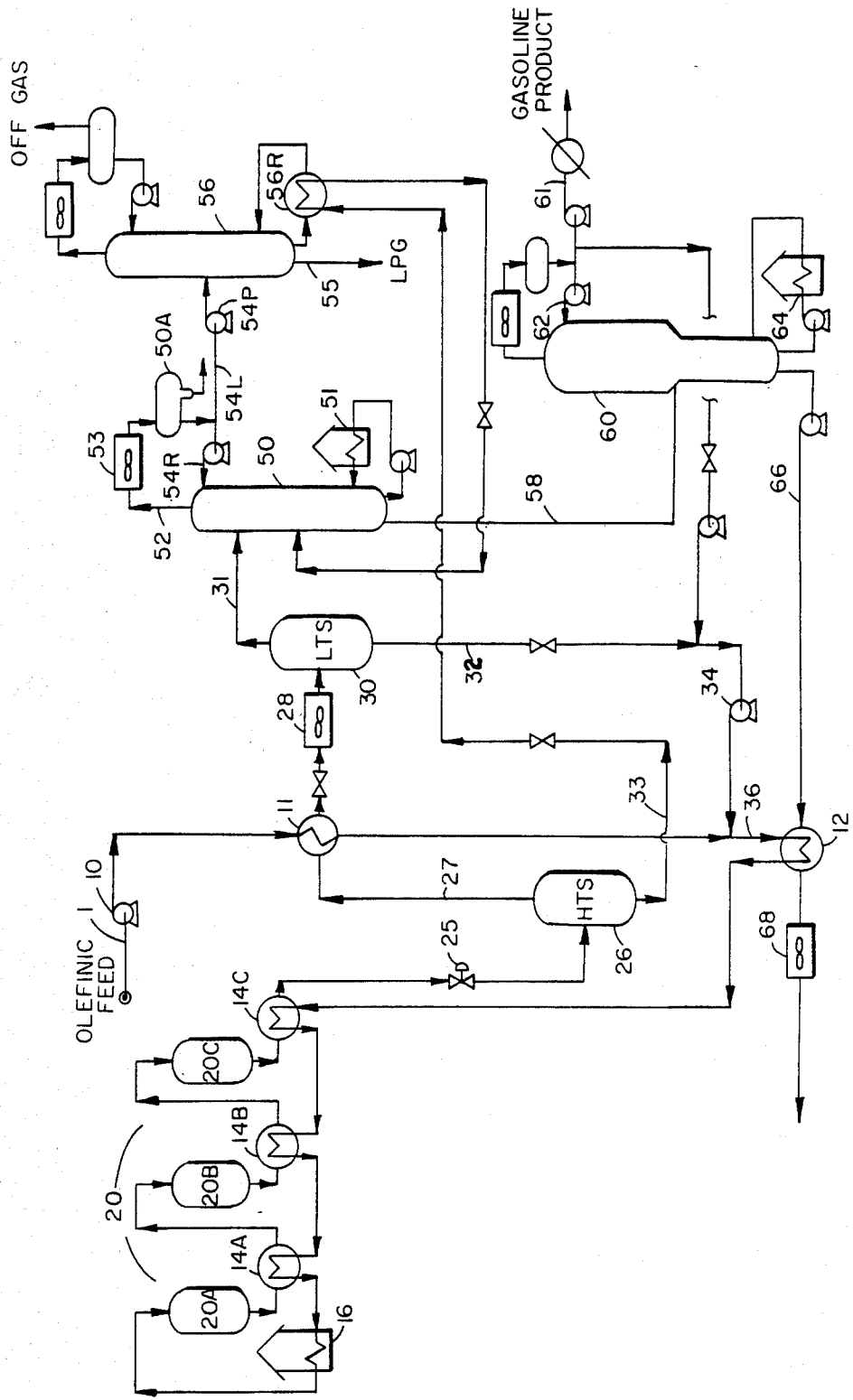

CATALYTIC CONVERSION OF OLEFINS TO HEAVIER HYDROCARBONS

FIELD OF INVENTION

This invention relates to a continuous technique for the manufacture of distillate range hydrocarbon fuels. In particular it provides a system for operating an olefins conversion plant wherein a oligomerization catalyst, such as crystalline zeolite of the ZSM-5 type, is employed for converting olefinic feedstocks containing $C_2$–$C_6$ alkenes at elevated temperature and pressure.

BACKGROUND OF THE INVENTION

Conversion of olefins to gasoline and/or distillate products is disclosed, for example, in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992 Garwood and Lee disclose the operating conditions for the Mobil Olefin to Gasoline/Distillate (MOGD) process for selective conversion of $C_3{}^+$ olefins to mainly aliphatic hydrocarbons. In a related manner, U.S. Pat. Nos. 4,150,062 and 4,211,640 (Garwood et al) discloses a process for converting olefins to gasoline components. Typically, the process recycles gas or liquid hydrocarbons from a high-temperature, medium-pressure separator downstream of the catalyst bed back into the reaction zone where additional olefins are converted to gasoline and distillate products. If the reaction of the olefins in converting them to distillate and gasoline is allowed to progress in the catalyst stream without any measures taken to prevent the accumulation of heat, the reaction becomes so exothermically accelerated as to result in excessive temperature which favors the production of undesired products.

In the process for catalytic conversion of olefins to heavier hydrocarbons by catalytic oligomerization using a medium pore shape selective acid crystalline zeolite, such as ZSM-5 type catalyst, process conditions can be varied to favor the formation of either gasoline or distillate range products. At moderate temperature and relatively high pressure, the conversion conditions favor aliphatic distillate range product having a normal boiling point of at least 165° C. (330° F.). Lower olefinic feedstocks containing $C_2$–$C_8$ alkenes may be converted; however, the distillate mode conditions do not convert a major fraction of ethylene. One source of olefinic feedstocks of interest for conversion to heavier fuel products is the intermediate olefin-rich light oil obtained from Fischer-Tropch conversion of synthesis gas.

It is a main object of this invention to provide a continuous processes devised for upgrading synthol light oil intermediate by olefins to a valuable heavy distillate fuel product. A typical feedstock consists essentially of $C_5$–$C_6$ mono-olefins with a minor amount of coproduced oxygenate from Fischer-Tropsch synthesis.

SUMMARY OF THE INVENTION

A continuous process has been found for converting a feedstock comprising lower olefins to form higher hydrocarbons comprising a major amount of distillate product. This process comprises the steps of: combining olefinic feedstock with a pressurized liquid diluent stream comprising a major fraction of $C_5{}^+$ olefins; contacting the diluted feedstock with a shape selective medium pore acid zeolite oligomerization catalyst under reaction conditions at elevated temperature in a pressurized reactor zone to convert olefins to heavier hydrocarbons; reducing pressure on reaction effluent in a first phase separation zone to flash volatile components into a first vapor phase stream and recover a heavy liquid stream from the first phase separation zone; condensing a portion of the first vapor phase stream by cooling and recovering a gasoline-rich to provide the dominant portion of a liquid olefinic recycle stream for combining with the feedstock; and fractionating the heavy liquid stream from the first phase separation zone to recover a major heavy distillate hydrocarbon liquid product stream, a minor gasoline liquid product stream and light hydrocarbons. A minor amount of gasoline liquid recycle may be provided via the secondary product fractionation system.

The recycle contains olefinic gasoline boiling range components which are further converted into distillate product. In conjunction with reactor operating conditions, the recycle composition and rate determine the distillate product boiling range and properties such as viscosity. Typically, the reactor effluent pressure is reduced from at least about 4000 kPa reactor pressure to not greater than about 1500 kPa in the phase separator. In a preferred embodiment a $C_3$–$C_6$ olefinic feedstock is combined with the olefinic recycle stream in a ratio of at least about 2 moles of recycle per mole feedstock olefin.

These and other objects and features of the invention will be understood from the following detailed description and drawings.

THE DRAWING

The single FIGURE is a schematic representation of a fixed bed reactor system and product separation system, showing process flow streams and unit operations.

DESCRIPTION OF THE PREFERRED EMBODIMENTS

The oligomerization catalysts preferred for use herein include the crystalline aluminosilicate zeolites having a silica to alumina ratio of at least 12, a constraint index of about 1 to 12 and acid cracking activity of about 160–200. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Patent No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable shape selective medium pore catalyst for fixed bed is H-ZSM-5 zeolite with alumina binder in the form of cylindrical extrudates of about 1–5 mm. Other pentasil catalysts which may be used in one or more reactor stages include a variety of medium pore (~5 to 9Å) siliceous materials such as borosilicates, ferrosilicates, and/or aluminosilicates disclosed in U.S. Pat. Nos. 4,414,423, 4,417,086, 4,417,087 and 4,417,088, incorporated herein by reference.

The flowsheet diagram of the figure shows the process relationships of the inventive process, depicting the conversion of the $C_3$–$C_6$ rich olefinic intermediate, two-stage phase separation and recycle. Heavy hydrocarbons are recovered by fractionation and may be sent to a conventional hydrotreating unit for product finishing.

The present invention provides a continuous economic process for converting lower olefins to heavier hydrocarbons. It is an object of the present invention to separate olefinic gasoline from reactor effluent in an efficient manner to provide a recycle stream rich in $C_5$ to $C_9$ gasoline range hydrocarbons and having only minor amounts of $C_4^-$ light hydrocarbon compounds or $C_{10}^+$ distillate range product. The gasoline recycle stream is obtained by a phase separation technique wherein the reactor effluent stream is cooled to condense heavy hydrocarbons, especially distillate materials, which are recovered in a heavy liquid product stream.

GENERAL PROCESS DESCRIPTION

The olefinic feedstock supply 1 is normally liquid and can be brought to process pressure by means of pump 10 and preheated by passing sequentially through a series of heat exchange means 11, 12 and reactant effluent exchangers 14C, B, A, and furnace 16 prior to entering the catalytic reactor system 20.

A typical distillate mode multi-stage reactor system 20 is shown. A multi-reactor system is employed with inter-zone cooling, whereby the reaction exotherm can be carefully controlled to prevent excessive temperature above the normal moderate range of about 230° to 345° (450°–650° F.). While process pressure may be maintained over a wide range, usually from about 2800 to over 10,000 kPa (400–1500 psia), the preferred pressure is about 4000 to 7000 kPa (600 to 1000 psia). The feedstock is heated to reaction temperature and carried sequentially through a series of zeolite beds 20A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.5 to 1.5. The heat exchangers 14A and 14B provide inter-reactor cooling and 14C reduces the effluent to flashing temperature. Control valve 25, operatively connected between the reactor section 20 and a first high temperature phase separator (HTS) unit 26 provides means for reducing the process pressure, thereby vaporizing volatile components of the effluent stream, such as unreacted lighter hydrocarbons, including the light and intermediate hydrocarbons, such as $C_1$ to $C_9$ aliphatics. The first separator 26 may be a vertical cylindrical vessel having a hooded tangential inlet to effect separation of the flashed effluent mixture. Overhead vapor is withdrawn through conduit 27, cooled indirectly by incoming feedstock in exchanger 11 and passed through air cooler 28 to condense a major amount of gasoline range hydrocarbons for recovery in the second phase separation unit 30, the low temperature separator (LTS). This condensed stream is withdrawn through conduit 32 to provide essentially all of the liquid olefinic recycle stream and pressurized by pump means 34 prior to combining with feedstock in conduit 36.

The use of high temperature and low temperature phase separators to provide three different streams having various amounts of heavy, intermediate and light hydrocarbons is a flexible technique for partial or primary fractionation of reactor effluent. While a specific example herein is operated to vaporize a major amount of the intermediate gasoline range hydrocarbons (e.g., $C_5$ to $C_9$ aliphatics) from the first HTS unit with the $C_4^-$ light hydrocarbons, it is technically feasible to adjust the HTS operating conditions with higher pressure and/or lower temperature to direct a major amount of the gasoline range material into the heavy liquid stream along with the $C_{10}^+$ distillate range hydrocarbons. Thus the intermediate range recycle stream can be obtained by further flashing of the HTS bottoms in a second phase separation zone.

In the preferred embodiment, the HTS unit 26 is maintained at sufficient temperature to vaporize substantially all of the $C_4^-$ light gas and a major amount of $C_5$–$C_9$ intermediates contained in the total reactor effluent. Prior to the serial LTS unit, temperature is decreased sufficiently to condense the $C_5$–$C_9$ recycle stream, while permitting the major amount of $C_4^-$ components to remain in the vapor phase for subsequent recovery of a minor amount of $C_5^+$ hydrocarbons in the secondary fractionation subsystem, beginning with the debutanizer tower 50. The present invention is a significant improvement over the system disclosed in U.S. Patent Application Ser. No. 400,828 filed July 22, 1982, now U.S. Pat. 4,444,988 which application describes the use of liquified $C_3$–$C_4$ recycle to control heat of reaction in converting olefins to gasoline. In the present system, an improvement in the operation of the phase separator and secondary fractionation units permits increased recovery of distillate range product, higher quality products and decreased cost of capital equipment and energy requirements.

Liquid hydrocarbons rich in distillate are recovered from the first phase separation zone 26 at flashing pressure, preferably about 1100 to 1500 kPa (160 to 220 psia) and passed via conduit 33 to debutanizer fractionation tower 50 after providing the energy to reboil the deethanizer bottoms in reboiler 56R at a lower stage therein where the heavy liquid contacts rising vapor from reboiler section 51 to vaporize dissolved lighter hydrocarbons, especially $C_4^-$ hydrocarbons present in the feedstock or generated during conversion. A vapor overhead stream from the second separation zone 30 is sent directly through conduit 31 to the debutanizer tower 50 at an intermediate stage. The debutanizer overhead stream 52 may be cooled by air cooler 53 to produce reflux 54 and recovered as LPG byproduct through conduit 55 from deethanizer 56. The overhead off-gas from the deethanizer may be routed through conduit 65 to the fuel gas system.

The amount of recycle can be varied according to need. Light hydrocarbons and byproduct water are withdrawn from the debutanizer overhead accumulate 50A. The debutanizer bottoms stream 58, which is a heavier hydrocarbon stream containing gasoline and distillate range material, is sent to product splitter 60 where the heavier hydrocarbons are fractionated to provide a condensed gasoline product stream 61 and condensed reflux 62. Splitter tower 60 has a furnace fired reboiler section 64 and the refined heavy distillate product is recovered through conduit 66, and cooled by incoming feedstock in exchanger 12 and in cooler 68. Advantageously, the distillate-rich liquid phase is fractionated to provide a major product stream consisting essentially of 154° C.+ aliphatic hydrocarbons comprising a major amount of $C_{10}$–$C_{20}$ aliphatic hydrocarbons. This product may then be hydrotreated in a separate process step (not shown) to provide a heavy distillate product having a viscosity of at least about 1.8 centistokes. Details of a mild hydrogenation treatment may be obtained from U.S. Pat. No. 4,211,640, incorporated by reference, typically using Co or Ni with W/Mo and/or noble metals.

In order to obtain heavy distillate product having a relatively high viscosity, higher reaction pressures and a heavier recycle stream are employed. For instance, if a 3 centistoke fuel product is required, a process pressure of at least 5500 kPa (800 psia) is suggested as well as more light distillate in the recycle stream.

There are several advantages to the process design. The intermediate range hydrocarbon recycle consists essentially of $C_5+$ hydrocarbons, with minor amounts of $C_4-$ components. This recycle material has a relatively high heat capacity and provides a good heat sink without diminishing feedstock olefin partial pressure and thereby maintaining a high olefin partial pressure at reactor inlet. The liquid recycle is economically repressurized by pumping, which requires modest power consumption. The debutanizer is operable at about 1000 kPa (150 psi) to condense all overhead without refrigeration, thus providing energy efficiency in obtaining the LPG byproduct. The product splitter tower can be operated at atmospheric pressure, thus improving separation between gasoline and distillate and holding the bottoms temperature to less than about 273° C. (525° F.) to provide raw distillate product stability.

A typical distillate mode oligomerization operation is conducted over a fixed bed of HZSM-5/alumina extrudate catalyst using the techniques described in U.S. patent application Ser. No. 488,834, filed April 26 1983, now U.S. Pat. No. 4,456,779 and U.S. Pat. No. 4,433,185 (Tabak), incorporated herein by reference. Reactor sequencing and catalyst regeneration are known in the art.

In the following example, an aliphatic feedstock containing 62 wt. % propene and butene, together with lower alkanes and very minor amounts of other olefins is pressurized (~5800 kPa), combined with recycle gasoline and heated to initial reaction temperature (~315° C.) and contacted with a series of reactors containing ZSM-5 catalyst under conditions to convert about 95% of the $C_3$-$C_4$ olefins (LHSV≃1). The hot effluent is precooled (285° C.) and flashed into the HTS unit at about 220° C. and 1340 kPa. The HTS overhead is further cooled to about 125° C. and separated in the LTS unit. The debutanizer tower is operated at about 1000 kPa provide $C_4-$ overhead at 43° C. and bottoms at 230° C. The atmospheric G/D splitter tower provides raw olefinic distillate and raw gasoline products and a minor portion of recycle as makeup. The deethanizer tower is operated at about 2100 kPa to provide product LPG, consisting essentially of $C_3$-$C_4$ aliphatic hydrocarbons, and an offgas usable as fuel.

Table I gives the composition of the major process streams for a distillate mode plant operated under steady state conditions. Table II gives product properties for raw and hydrotreated liquid fuels. Data are given in parts by weight and metric units unless otherwise stated.

TABLE I

STREAM COMPOSITION
MASS FLOW PER 100 PARTS FRESH FEED BASIS:

| COMPONENTS (WT %) | FRESH FEED | GASOLINE RECYCLE | REACTOR EFFLUENT | HTS BOTTOMS | HTS OVERHEAD | LTS OVERHEAD | LTS BOTTOMS |
|---|---|---|---|---|---|---|---|
| METHANE | 0.0 | .0 | .0 | .0 | .0 | .0 | .0 |
| ETHENE | 0.1 | .0 | .0 | .0 | .0 | .0 | .0 |
| ETHANE | 0.6 | 0.1 | 0.8 | .0 | 0.8 | 0.7 | 0.1 |
| PROPENE | 26.6 | 0.5 | 1.8 | 0.1 | 1.7 | 1.3 | 0.5 |
| PROPANE | 10.5 | 4.5 | 16.6 | 0.6 | 16.0 | 11.5 | 4.5 |
| I-BUTANE | 20.3 | 13.1 | 34.5 | 1.9 | 32.6 | 19.6 | 13.0 |
| I-BUTENE | 35.4 | 1.2 | 3.0 | 0.2 | 2.8 | 1.6 | 1.2 |
| N—BUTANE | 5.5 | 5.1 | 11.8 | 0.7 | 11.1 | 6.1 | 5.0 |
| I-PENTANE | 0.6 | 5.5 | 6.2 | 0.5 | 5.6 | 2.4 | 3.2 |
| I-PENTENE | 0.4 | 5.7 | 6.3 | 0.6 | 5.8 | 2.4 | 3.4 |
| N—PENTANE | .0 | 0.2 | 0.3 | .0 | 0.2 | 0.1 | 0.2 |
| 125-330 GASO | 0.0 | 108.1 | 116.4 | 28.7 | 87.7 | 10.7 | 77.0 |
| 330 + DIST | 0.0 | 25.8 | 72.4 | 47.8 | 24.6 | 0.4 | 24.2 |

| COMPONENTS (WT %) | DEC4 BOTTOMS | GASOLINE PRODUCT | DIST PRODUCT | DEC2 OFFGAS | DEC2 BOTTOMS | MAKEUP GASOLINE RECYCLE |
|---|---|---|---|---|---|---|
| METHANE | 0.0 | 0.0 | 0.0 | .0 | 0.0 | 0.0 |
| ETHENE | 0.0 | 0.0 | 0.0 | .0 | 0.0 | 0.0 |
| ETHANE | 0.0 | 0.0 | 0.0 | 0.7 | 0.0 | .0.0 |
| PROPENE | 0.0 | 0.0 | 0.0 | 0.3 | 1.1 | 0.0 |
| PROPANE | 0.0 | 0.0 | 0.0 | 1.2 | 10.9 | 0.0 |
| I-BUTANE | 0.1 | .0 | 0.0 | 0.2 | 21.3 | .0 |
| I-BUTENE | .0 | .0 | 0.0 | .0 | 1.8 | .0 |
| N—BUTANE | 0.2 | .0 | 0.0 | .0 | 6.7 | 0.1 |
| I-PENTANE | 2.7 | 0.5 | 0.0 | 0.0 | 0.2 | 2.2 |
| I-PENTENE | 2.8 | 0.5 | 0.0 | 0.0 | 0.1 | 2.3 |
| N—PENTANE | 0.1 | .0 | 0.0 | 0.0 | .0 | 0.1 |
| 125-330 GASO | 39.4 | 6.9 | 0.8 | 0.0 | 0.0 | 31.6 |
| 330 + DIST | 48.2 | 0.3 | 46.3 | 0.0 | 0.0 | 1.5 |

TABLE II

| | TYPICAL PRODUCT PROPERTIES | | |
|---|---|---|---|
| | $C_6$-330° F. (166° C.) | 330° F. (166° C.) + Distillate | |
| Properties | Gasoline | Raw | Hydrotreated |
| Gravity, °API | 62.8 | 48.1 | 49.6 |
| Total Sulfur, ppmw | 0 | 0 | 0 |
| Octane Number, R + O | 92 | — | — |
| Bromine Number | — | 73.0 | 2.0 |
| Weight % $H_2$ | — | 14.3 | 15.1 |
| Aniline Pt | — | 163 | 193 |
| Freeze Pt (°F.) | — | <−76 | <−76 |
| Cetane Number | — | 35 | 52 |
| Luminometer Number | — | 69 | 99 |

During operation of the HTS-LTS phase separator series, it may be desirable to change the operating pressure or temperature to accomodate process variation or equipment design. It is understood that satisfactory phase separation of the various boiling range streams can be achieved by lowering the separator pressure with corresponding decreasing temperature. Using the same effluent as in the above example (Table I), the following tabulated data sets forth a series of paired conditions to effect a satisfactory stream composition for each of the heavy liquid HTS bottoms, intermediate LTS bottoms and light LTS overhead.

TABLE III

| High Temperature Separator (HTS) | | Low Temperature Separator (LTS) | |
|---|---|---|---|
| Pressure (kPa) | Temperature (0° C.) | Pressure (kPa) | Temperature (0° C.) |
| 1240 | 215–221 → | 1100 | 120–130 |
| 1035 | 190–205 → | 965 | 110–120 |
| 690 | 160–180 → | 620 | 80–90 |
| 520 | 130–150 → | 450 | 60–70 |
| 415 | 130–150 → | 345 | 50–60 |

Various modifications can be made to the system, especially in the choice of equipment and non-critical processing steps. While the invention has been described by specific examples, there is no intent to limit the inventive concept as set forth in the following claims.

What is claimed is:

1. A continuous process for converting a feedstock mixture comprising lower olefins to form higher hydrocarbons comprising a major amount of distillate product comprising the steps of:

combining olefinic feedstock with a pressurized liquid diluent stream comprising a major fraction of $C_5+$ olefins;

contacting the diluted feedstock with a shape selective medium pore acid zeolite oligomerization catalyst under reaction conditions at elevated temperature in a pressurized reactor zone to convert olefins to heavier hydrocarbons;

reducing pressure on reaction effluent in a first phase separation zone to flash volatile components into a first vapor phase stream and recovering a heavy liquid stream from the first phase separation zone;

condensing a portion of the first vapor phase stream by cooling and recovering a gasoline-rich liquid stream to provide the dominant portion of a liquid olefinic recycle stream for combining with the feedstock; and fractionating the heavy liquid stream from the first phase separation zone to recover a heavy distillate hydrocorbon major liquid product stream, a minor gasoline liquid product stream and light hydrocarbons.

2. The process of claim 1 wherein reactor effluent pressure is reduced from at least about 4000 kPa reactor pressure to not greater than about 1500 kPa in the first phase separation zone.

3. The process of claim 2 wherein feedstock comprising a major amount of $C_3$–$C_6$ olefin is combined with the olefinic recycle stream in a ratio of at least about 2 moles of recycle per mole of feedstock olefin and contacted with a fixed bed of acid aluminosilicate zeolite catalyst having a constraint index of about 1 to 12 at a reaction temperature of about 230° C. to 345° C. at process pressure of about 4000 to 7000 kPa to convert a major amount of feedstock olefins.

4. The process of claim 1 wherein the distillate-rich heavy liquid stream is further fractionated to provide a major product stream consisting essentially of about 154° C.+ aliphatic hydrocarbons comprising a major amount of $C_{10}$–$C_{20}$ aliphatic hydrocarbons, and to provide a minor amount of gasoline range hydrocarbons.

5. The process of claim 4 further comprising the step of hydrotreating said distillate product stream to provide a heavy distillate product having a viscosity of at least about 1.8 centistokes.

6. The process of claim 4 wherein a portion of said gasoline range hydrocarbons is recycled with the dominant gasoline-rich recycle stream.

7. The process of claim 1 wherein the heavy liquid stream from the first phase separation zone and uncondensed vapor from a second phase separation zone are further fractionated in a secondary debutanizer tower to recover a $C_4-$ light gas and a $C_5+$ liquid product stream; and further including the step of fractionating said $C_5+$ liquid product stream in a gasoline-distillate product splitter tower.

8. A catalytic process for converting an olefinic feedstock comprising lower olefin to heavier hydrocarbon product comprising the steps of:

contacting the feedstock and a recycled hydrocarbon with shape-selective zeolite oligomerization catalyst in catalytic reaction zone at elevated temperature and pressure to provide a heavier hydrocarbon effluent stream comprising heavy, intermediate and light hydrocarbons;

flashing the effluent stream between the reaction zone and a phase separation zone by reducing pressure of the effluent stream, thereby producing a heavy liquid stream rich in heavy hydrocarbons and a flashed effluent vapor stream containing lighter hydrocarbons;

separating and recovering a recycle stream rich in intermediate range hydrocarbons from the separation zone and pressurizing the recycle stream for recycle to the reactor inlet;

further fractionating the heavy liquid stream and flashed effluent vapor from the phase separation zone in first distillation tower to remove light hydrocarbons therefrom; and recovering substantially all of the heavy hydrocarbons produced in the reaction zone in a fractionated liquid product stream.

9. The process of claim 8 wherein the oligomerization catalyst comprises a shape-selective medium pore crystalline aluminosilicate zeolite having a silica:alumina mole ratio of at least 12 and a constraint index of about 1 to 12.

10. The process of claim 8 wherein the catalyst comprises H-ZSM-5 having an acid cracking activity of about 160 to 200, and the olefinic feedstock comprises at least 50 mole % $C_3$ to $C_6$ olefins.

* * * * *